United States Patent [19]

Hansen et al.

[11] 3,952,919

[45] Apr. 27, 1976

[54] RESERVOIR ADAPTER FOR LIQUID DISPENSER

[75] Inventors: John Erik Hansen, Arvada, Colo.; Joseph M. Magrath, McCook, Nebr.; Leonard L. Hierath, Denver, Colo.

[73] Assignee: Joseph M. Magrath, McCook, Nebr.

[22] Filed: July 3, 1975

[21] Appl. No.: 593,128

[52] U.S. Cl. .............................. 222/89; 141/329; 285/320; 128/218 G
[51] Int. Cl.² .......................................... B67B 7/26
[58] Field of Search ............... 141/329, 330, 19; 285/320, 319, 317; 128/214.2, 221, 218 G; 222/80–83, 89, 91, 92, 105, 211

[56] References Cited
UNITED STATES PATENTS

| | | | |
|---|---|---|---|
| 1,324,206 | 12/1919 | Nickell | 222/83 |
| 2,860,820 | 11/1958 | Falligant | 222/82 |
| 3,092,291 | 6/1963 | Franck | 222/83 |

Primary Examiner—Robert B. Reeves
Assistant Examiner—H. Grant Skaggs

[57] ABSTRACT

An adapter for attaching and sealing a liquid supply reservoir on a liquid dispenser of the metering type comprises a reservoir receiving body and a detachable element for securing the body to a dispenser with a seal piercing needle in position to receive the contents of the reservoir. A pivoted clamp is provided for clamping the reservoir on the body when the seal has been pierced and holds the reservoir securely to the body during use of the dispenser. A nut secures the detachable element on the dispenser, a spring bias being provided to afford adjustment of the element with respect to the nut. A check valve is provided to prevent return of liquid to the reservoir and facilitates the use of collapsible supply reservoirs.

9 Claims, 6 Drawing Figures

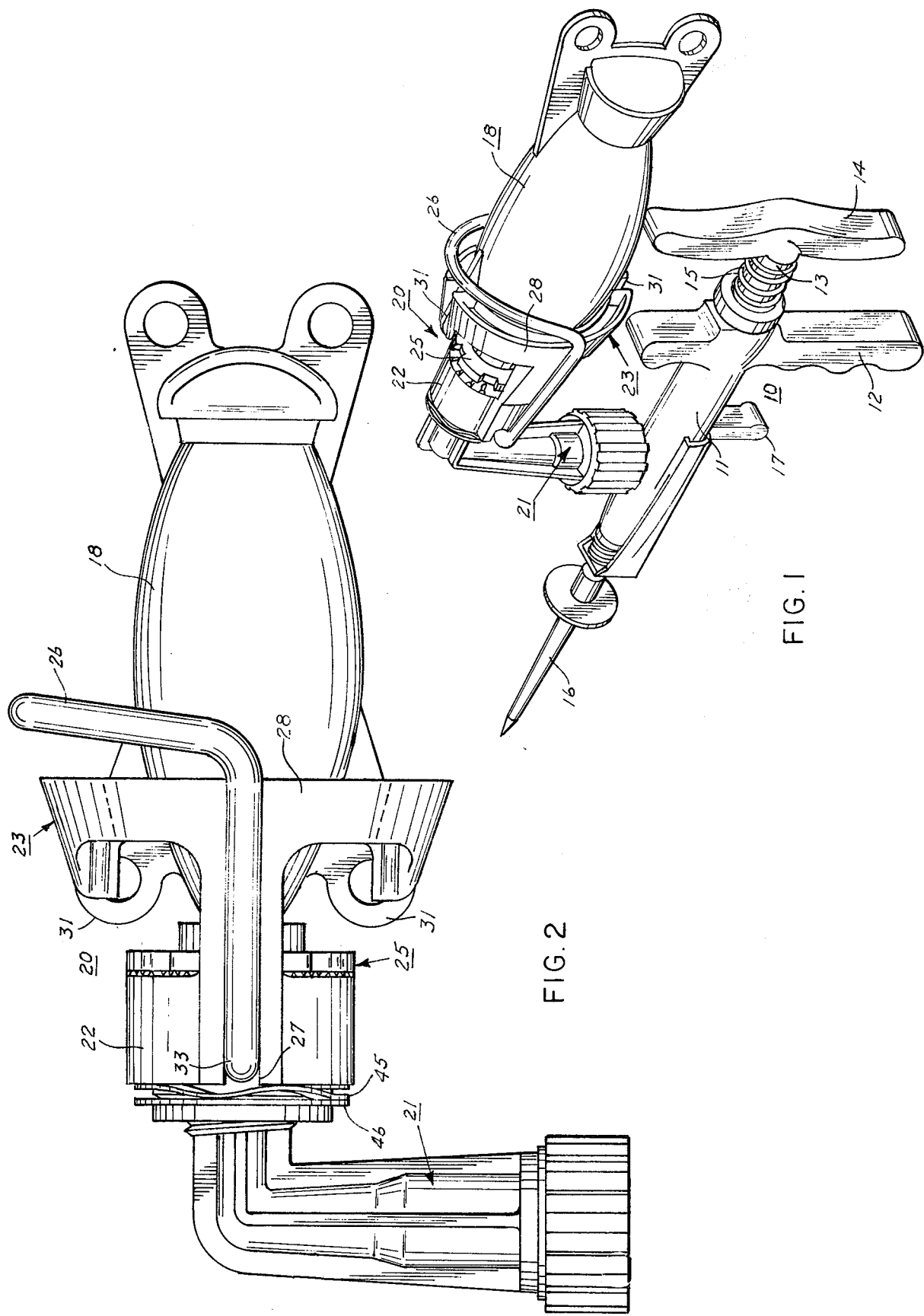

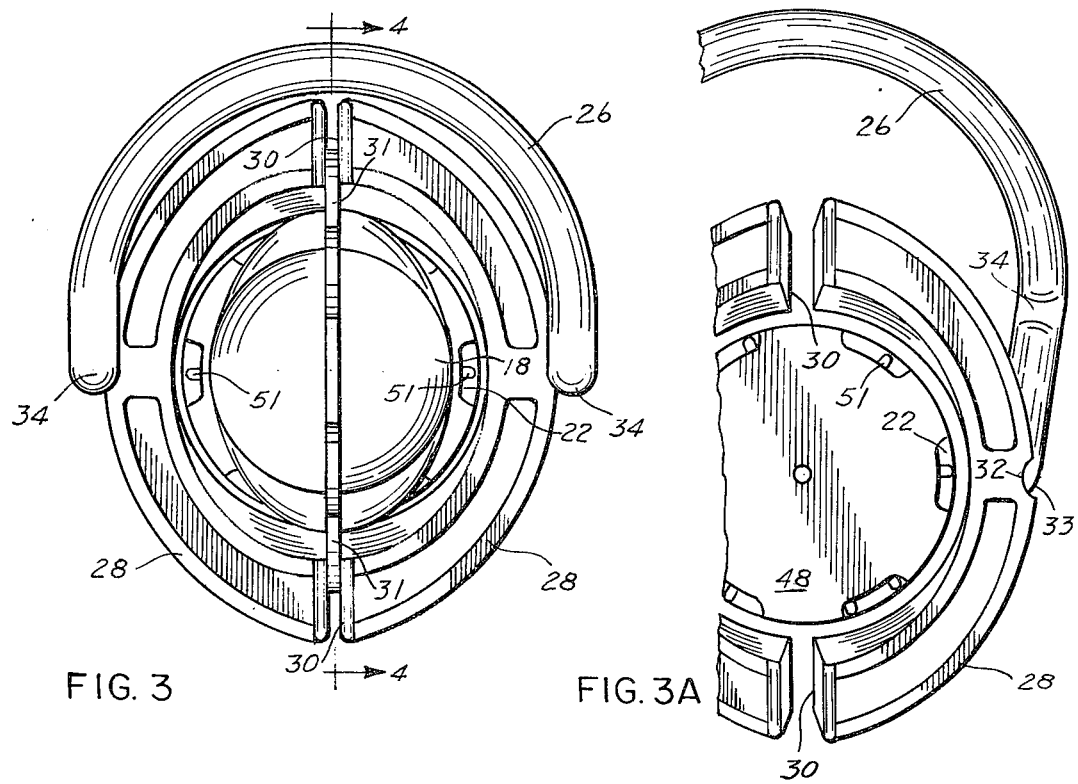
FIG. 3
FIG. 3A
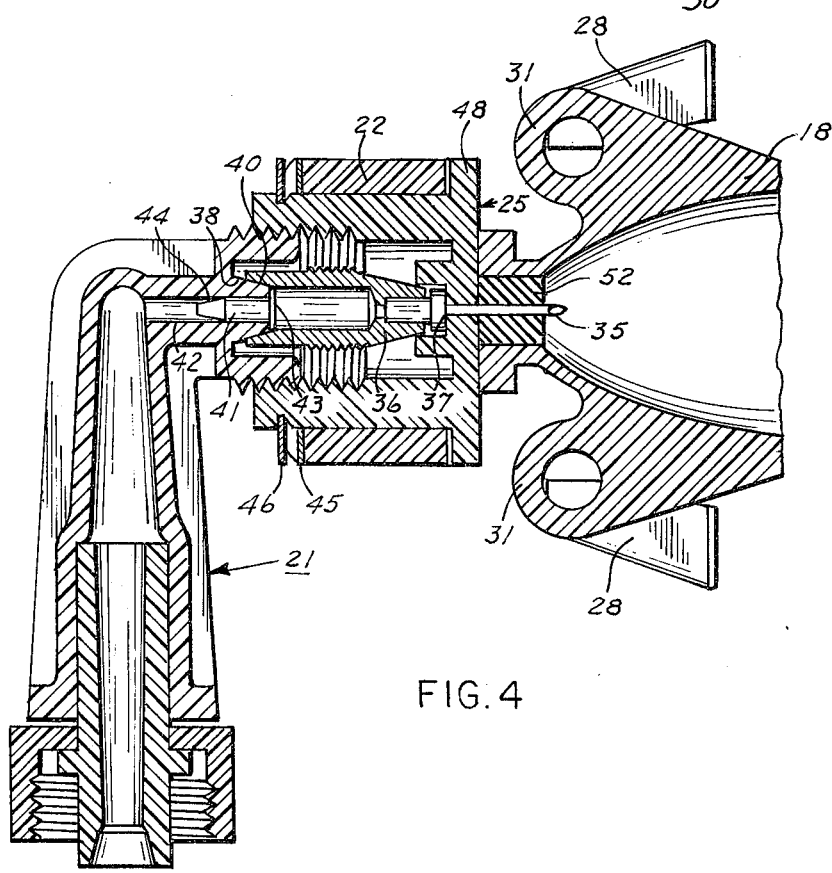
FIG. 4

RESERVOIR ADAPTER FOR LIQUID DISPENSER

This invention relates to liquid dispensers of the metering type and particularly to an improved adapter for mounting collapsible reservoirs on such devices for facilitating the use of such reservoirs for repeated operations of the dispenser.

By way of example, a repeated operation dispenser is shown and described in U.S. Pat. No. 3,827,601 issued Aug. 6, 1974.

Liquid dispensers of the repeated operation metering type are employed, for example, in the field of veterinary medicine for dispensing medicinal liquids to a number of animals one after another. It is important that such dispensing operations be accurately and easily performed to assure that each animal receives the required amount of medicine with minimum interruption of the dispensing procedures. Collapsible containers have been provided for liquid medicines and have been found useful in the veterinary field. These containers are provided with stoppers or seals which may be pierced by sharp hollow needles in order to draw out the contained liquid, the container collapsing as the liquid is withdrawn. The container walls are relatively stiff and tend to return from their collapsed position when air is allowed to enter after removal of the liquid. The use of such containers for dispensing devices of the repeated operation type is desirable, and, accordingly, it is an object of this invention to provide a simple and easily operated device for detachably securing such containers to dispensing devices.

It is another object of this invention to provide an improved arrangement for attaching a liquid supply reservoir to a dispenser of the hand held metering type.

It is another object of this invention to provide an improved device for attaching a liquid supply reservoir to a hand held dispenser which affords quick and secure mounting of a collapsible wall reservoir on the dispenser.

Briefly, in carrying out the objects of this invention in one embodiment thereof, a reservoir attaching device is constructed for mounting on a hand held liquid dispenser which provides a piercing needle in position to pierce the stopper or seal of a liquid reservoir for effecting a discharge of liquid from the reservoir to the device. The mounting includes jaws arranged to clamp the reservoir firmly in position upon manipulation of a spring bail for clamping jaws about a portion of the reservoir when it is in position with the seal pierced by the discharge needle. The clamp jaws are arranged to seize and firmly compress ears or legs on the reservoir to prevent displacement of the seal and needle and afford complete discharge of the contained liquid. A check valve in the mounting prevents the return of fluid to the reservoir through the hollow discharge needle. The clamp may be released quickly and the reservoir replaced by another when it is empty.

The features of novelty which characterize this invention are pointed out with particularity in the claims annexed to and forming a part of this specification. The invention itself, however, together with further objects and advantages thereof, may best be understood from the following description taken in connection with the accompanying drawings in which:

FIG. 1 is a perspective view of a liquid dispenser of the hand held type having a reservoir attaching device embodying the invention;

FIG. 2 is a side elevation view of the attaching device in clamped position;

FIG. 3 is a right hand end view of the device of FIG. 2;

FIG. 3a is a partial view of the device viewed as in FIG. 3 shown in unclamped position;

FIG. 4 is a sectional view of the device taken along the line 4—4 of FIG. 3; and, FIG. 5 is an exploded view showing the parts of the device.

Figure 5:
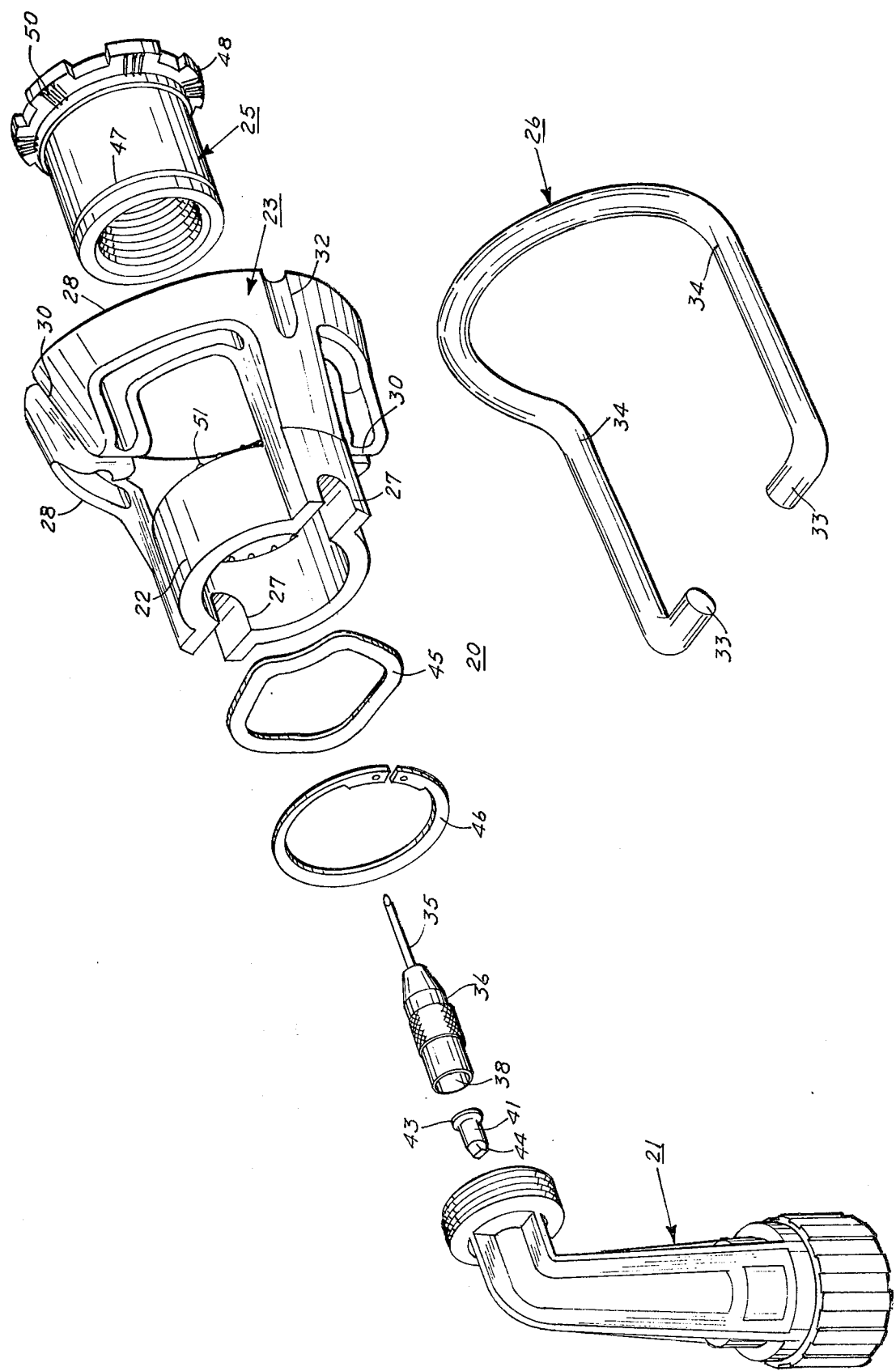

Referring now to the drawings, the dispenser illustrated at 10 in FIG. 1 is of the type disclosed in the above patent and comprises an elongated body 11 having a handle 12 and a discharge plunger 13 having a handle 14. The plunger 13 is biased outwardly by a return spring 15. A discharge nozzle or cannula 16 is removably attached to the outlet of the dispenser and may be removed after use by forward sliding movement of a release member 17 which ejects the cannula.

A flexible, readily collapsible reservoir or container 18 is mounted on the body 10 by use of a clamping device 20 embodying the invention.

The clamping device as shown in FIGS. 2 through 5 includes an adapter or fitting 21 and a mounting member 22 which is an integral part of a clamping head 23. The member 22 is securely attached to the fitting 21 by a threaded collar 25 which also secures the piercing needle in position as described below. The reservoir 18 is clamped to the head 23 by operation of a spring or bail 26 which is pivoted on the head 23 in slots 27 at its end opposite the reservoir 18 and is retained in grooves or slots 32 at its end adjacent the reservoir when in its clamping position.

The fitting 21 is a right angle connection and the reservoir is thus positioned in general alignment with the body 11 of the dispenser. In this position the flexible reservoir 18 thus lies above the operator's hand in alignment with his arm and with the direction of the path of liquid discharged from the dispenser. This position of the reservoir reduces the liklihood of interference with the operator's movements and his positioning of the dispenser during the treatment of an animal.

The head 23 comprises two semi-circular jaw members 28 which are separated by gaps 30 arranged to receive lugs or tabs on the reservoir which are indicated at 31 in FIGS. 1, 2 and 4.

In the released or unclamped position the faces of the jaw members of each pair slope slightly away from each other as shown in FIG. 3a. When the bail 26 is applied by moving it downwardly over the arcuate sides of the jaws 28 the arms of the jaws are rotated slightly inwardly and bring the faces into parallel with one another for clamping the lugs 31 as shown in FIG. 3.

When the bail 26 is in its clamping position as shown in FIGS. 1, 2 and 3, it is retained in the slots or grooves 32 on each side in the jaw members 28, one of the grooves being shown clearly in FIG. 5. This holds the lugs 31 securely to clamp the lugs and hold the container 18 in position. The dispenser then may be manipulated as required without displacing the reservoir.

The bail 26 is formed to provide inturned ends 33 which rotate in the slots when the bail is moved into and out of its clamping position. When the reservoir 18 is placed on the dispenser with the lugs 31 between the jaws 28 in the slots 30, the bail is rotated to press its sides 34 downwardly from the position in FIG. 3a over the arcuate outer surfaces of the jaw members.

The arcuate bow of the bail spaces the ends 34 apart a distance less than the spacing of the grooves 32 of the jaw members and resiliently presses the jaw members together when in the clamping position. The resilience of the bail thus allows it to be moved readily in and out of the clamping position and locks it in position in the grooves 32 to prevent accidental release.

As shown in FIGS. 4 and 5, the clamping device is provided with a seal piercing hollow needle 35 mounted on a block or hub 36. The hub is secured on the fitting 21 by tightening the threaded collar 25 onto the fitting, an annular shoulder 37 on the collar being pressed against a conical section of the hub 36. This seats an internal conical surface 38 on the hub against a conical nipple 40 in the fitting 21 and seals the needle on the fitting. A check valve 41 is positioned in a passage 42 by a press fit and prevents reverse flow of fluid. This valve has been illustrated as of the resilient "duck bill" type comprising a cylindrical body of resilient plastic having a collar 43 at its inlet end and a flattened discharge end 44. The flattened end 44 is normallly closed, but opens when fluid under pressure flows from the reservoir into the body 41 of the valve. Upon reverse pressure the flattened end prevents reverse flow of the fluid.

The collar 25 is rotatably secured in the mounting member 22 by moving it into the member from right to left as viewed in FIG. 5, until it protrudes from the member and then placing a spring washer 45 of the undulating type over the protruding end of the collar and locking the collar in place with a spring ring 46 which acts as a stop. The ring 46 is seated in a slot 47 in the outer surface of the collar. The collar is provided with a flange 48 which engages the right hand surface of the mounting member 22. The face of the flange 48 and the engaging face of the member 22 are provided with projections or are knurled or otherwise roughened to provide high friction engaging surfaces indicated at 50 and 51, respectively. These surfaces are pressed together by the resilience of the spring washer 45 and prevent relative rotation of the collar 25 and the member 22, but allow compression of the spring 45 to afford turning of the collar 48 when attaching the clamping device to the fitting 21. When the collar 25 has been set in position on the fitting 21 the member 22 is released so that the spring washer 45 presses the friction surfaces 50 and 51 into engagement and prevents relative rotation of the collar and member. For purposes of illustration the surfaces 50 and 51 are shown as having interfitting projections.

During the use of the dispenser, after the adapter has been mounted on the dispenser as shown in FIG. 1, a flexible reservoir or container 18 is provided; the bail 26 is released from its clamping position and the container is pressed into position. This forces the needle 35 to pierce the seal or cork of the container indicated at 52 in FIG. 4; the lugs 31 are at the same time positioned between the clamping jaws. The bail 26 is then moved into clamping position and the container 18 is thus secured ready for use. The dispenser is then operated to remove any air present and the passages in the fitting and dispenser are thus filled with liquid and the dispenser is ready for use.

As the dispenser is used, liquid is withdrawn from the container and the walls of the container gradually collapse accordingly. No liquid can return to the container, this being prevented by the check valve 41. When the container has been emptied it is removed by releasing the bail 26 and drawing the container away from the needle 35. Liquid may be retained in the needle and entrance passage of the fitting, and the device may be held upright, with the needle pointing vertically upward to minimize the loss of liquid while replacing the container with a new container.

The adapter is particularly useful in the field when a large number of animals are to be treated and facilitates the treatment of such animals within a minimum time. The ease of replacing the containers and the positive clamping and mounting of the containers assures highly effective use of flexible containers under difficult as well as normal treatment conditions.

While the invention has been illustrated and described in connection with a single embodiment, other applications and embodiments will occur to those skilled in the art. Therefore it is not desired that this invention be limited to the details illustrated and it is intended by the appended claims to cover all embodiments which fall within the spirit and scope of the invention.

We claim:

1. An adapter for connecting a closed collapsible liquid supply reservoir to a liquid metering dispenser of the repeating type comprising:
    a fitting having a passage therethrough for connection to the inlet of a dispenser;
    a hollow needle having a seal piercing end;
    means for mounting said needle on said fitting in communication with the passage therein, said means including a nut threaded on said fitting for securing said needle on the fitting with said seal piercing end extending axially beyond said nut;
    a clamping member mounted on said nut and having jaw members adjacent said piercing end for receiving and holding a supply reservoir; and,
    movable locking means mounted on said adapter for moving said jaw members into clamping position and locking them, to hold the supply reservoir securely against said nut.

2. The invention set forth in claim 1 wherein said fitting includes a first portion for attachment to the dispenser and a second portion extending normal thereto and toward the rear of the dispenser.

3. The invention set forth in claim 1 wherein said clamping means comprises a resilient metal bail pivoted on said clamping member adjacent said nut and extending rearwardly for engagement with said jaw members and for urging said jaw members toward one another and means for retaining said bail in clamping position.

4. The invention of claim 3 wherein said bail has elongated side members and a laterally extending arcuate bow portion connecting said side members and said means for retaining said bail comprises recesses in the sides of said jaws.

5. The invention of claim 1 wherein said clamping member comprises a cylindrical end for mounting rotatably on said nut, and said jaw members comprise axially and outwardly extending arms having generally C-shaped members at their outer ends, said C-shaped members opening toward one another and terminating in oppositely facing ends constituting jaw faces and spaced from one another, said locking means urging said faces toward one another in its clamping position.

6. The invention of claim 5 wherein said nut is cylindrical and has an outwardly extending flange at one end, said nut being insertable in the cylindrical portion of said clamping member with said flange at the inner end thereof adjacent said arms, and detachable means for securing said nut within said cylindrical member in rotatable relationship.

7. The invention of claim 6 including a spring member for positioning between or about said nut between said detachable securing means and the outer end of said cylindrical portion for holding said flange in frictional engagement with said cylindrical portion and for affording limited axial movement of said cylindrical portion of said nut, said spring member being compressible to afford rotation of said nut within said cylindrical portion.

8. The invention of claim 7 wherein said flange and the inner end of said cylindrical portion include high friction faces for preventing relative rotation when urged into engagement by said spring member.

9. The invention of claim 8 wherein said high friction faces comprise interfitting projections on the opposing faces of said flange and said cylindrical member.

* * * * *